United States Patent [19]

Albert

[11] 4,409,983
[45] Oct. 18, 1983

[54] PULSE MEASURING DEVICE

[76] Inventor: David E. Albert, Box 2700 - DUMC, Durham, N.C. 27710

[21] Appl. No.: 294,487

[22] Filed: Aug. 20, 1981

[51] Int. Cl.³ .............................................. A61B 5/02
[52] U.S. Cl. .................................... 128/690; 128/689
[58] Field of Search ...................... 128/687, 689–690, 128/639, 644

[56] References Cited

U.S. PATENT DOCUMENTS

| | | | |
|---|---|---|---|
| 2,658,505 | 11/1953 | Sheer | 128/672 X |
| 3,176,681 | 4/1965 | Smith | 128/687 |
| 3,717,140 | 2/1973 | Greenwood | 128/689 |
| 3,868,954 | 3/1975 | Ueda | 128/687 |
| 3,903,873 | 9/1975 | Royal et al. | 128/689 |
| 4,052,979 | 10/1977 | Scherr et al. | 128/690 |
| 4,129,124 | 12/1978 | Thalmann | 128/690 X |
| 4,159,416 | 6/1979 | Brejnik et al. | 128/690 X |
| 4,195,642 | 4/1980 | Price et al. | 128/689 |
| 4,198,988 | 4/1980 | Cash, Jr. et al. | 128/690 X |
| 4,245,648 | 1/1981 | Trimmer et al. | 128/689 X |
| 4,295,472 | 10/1981 | Adams | 128/690 |

FOREIGN PATENT DOCUMENTS 2717747 12/1977 Fed. Rep. of Germany ...... 128/690
2736377 2/1978 Fed. Rep. of Germany ...... 128/690
1312107 4/1973 United Kingdom ............... 128/690

Primary Examiner—Lee S. Cohen
Assistant Examiner—Angela D. Sykes
Attorney, Agent, or Firm—Richard H. Stern

[57] ABSTRACT

A portable, body-worn pulsemeter which displays the wearer's pulse rate by processing signals corresponding to the pulse beat of the wearer. This device has a piezoelectric transducer adapted to produce an output signal responsive to the force produced by the wearer's pulsebeat. The output signal operates through other elements to produce a representation of the wearer's pulse rate at the display. The transducer has a piezo-bender element to which a transducer post is affixed, the post being adapted to contact the wearer's skin in the vicinity of an artery. The piezo-bender element is elastically mounted to a housing element that is maintained in firm contact with the wearer's skin, and the physical constants of the elastic mounting are selected to filter out higher frequency components of the forces applied to the transducer post, thereby greatly reducing extraneous noise. Multiple transducer arrays and circuitry are disclosed, which further eliminate noise from the displayed pulse reading.

14 Claims, 19 Drawing Figures

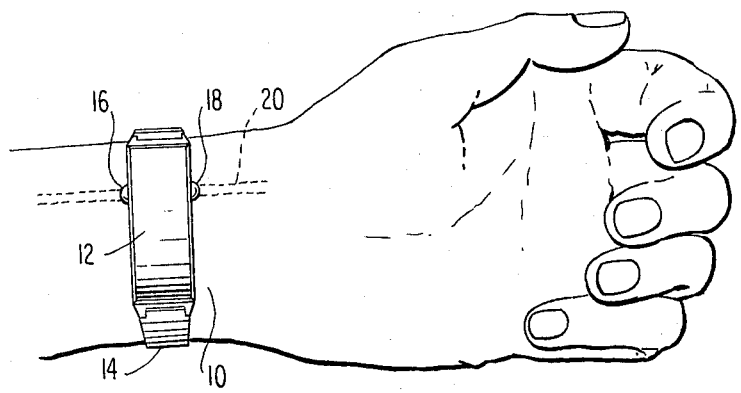
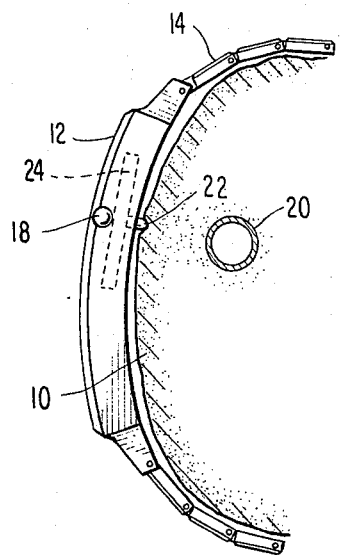
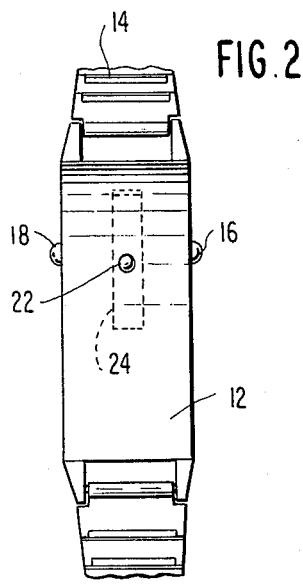
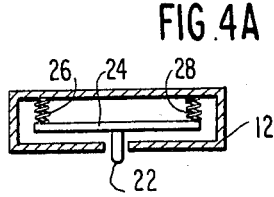
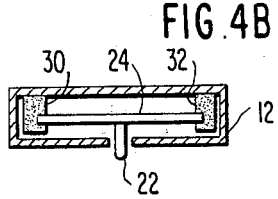
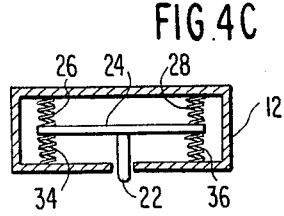
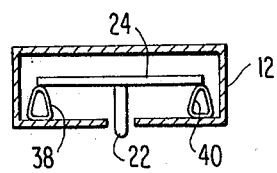
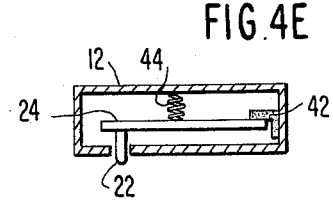
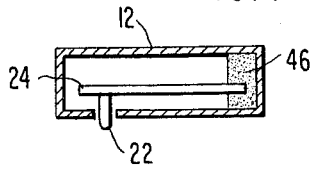
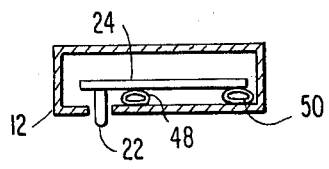
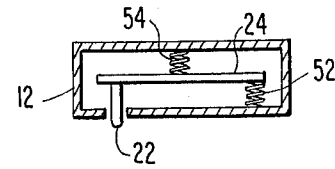

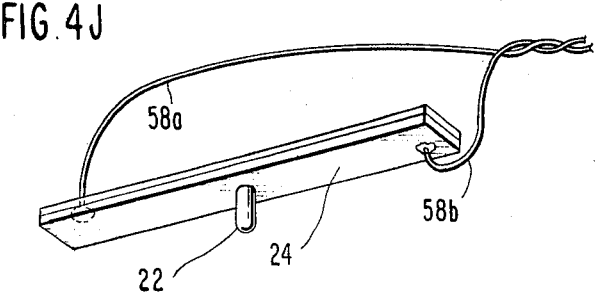
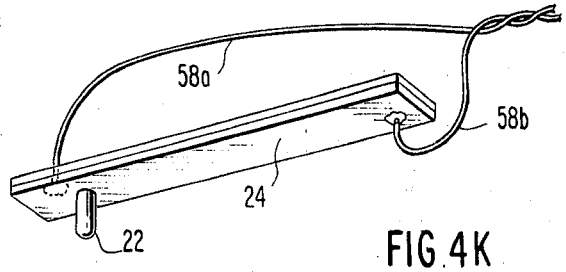
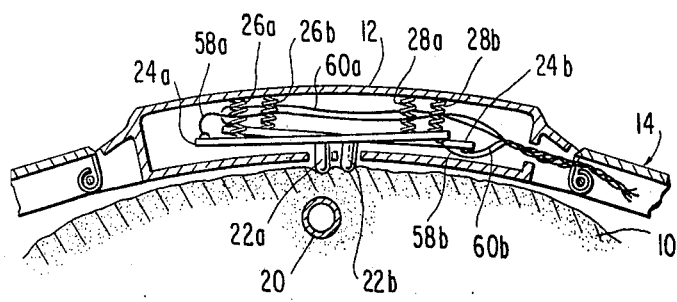
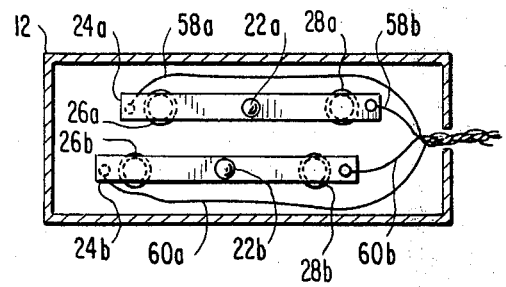
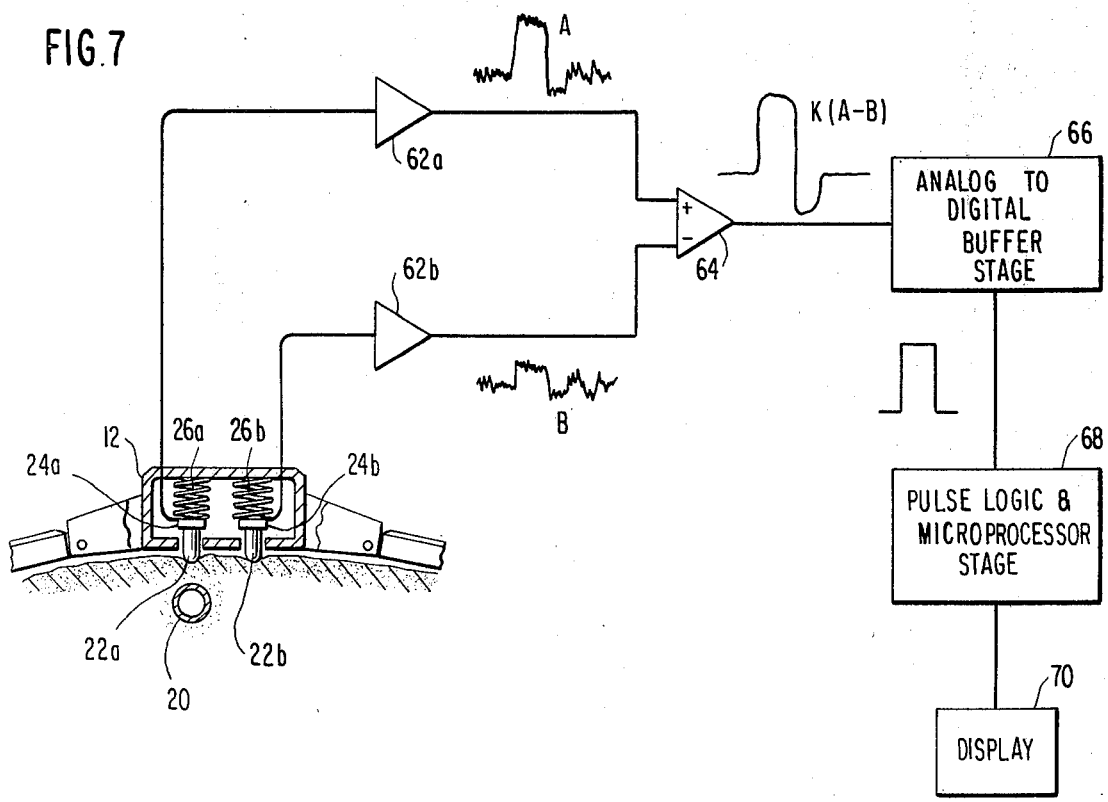

PULSE MEASURING DEVICE

BACKGROUND OF THE INVENTION

1. Field of the Invention

The present invention concerns a pulse measurement device. More particularly, it concerns an improved, portable, wearable mechanism for obtaining a relatively noise-free measurement of human pulse rate, under conditions of motion or other activity that tends to create severe noise in the signal. uch a device may be termed a "wristwatch pulsemeter."

2. Brief Discussion of the Prior Art

Several devices have been proposed for providing a wristwatch type of pulsemeter. One type of such device is the digital plethysmograph described in Prinz U.S. Pat. No. 4,120,296, which customarily utilizes an infrared light transducer. Others have proposed using piezoelectric or other pressure sensitive transducers, such as in Stupay U.S. Pat. No. 4,059,118, which uses an "actuator" pin pressing against a piezoelectric crystal.

Typically, such devices tend to have several shortcomings. Those using an optical transducer, such as the digital plethysmographs, consume substantial power in their light-emitting elements, and thus use up their battery life rapidly. Those devices suggesting use of piezoelectric transducers, such as Stupay, typically devote little attention to the substantial noise problem that attends use of such transducers in this application.

When such a pulsemeter is mounted on the wearer's body, as in a wristwatch device, the pulse signal is to a substantial extent masked by concurrent noise signals due to body motions. The mechanical transducer responds both to pressure from the wearer's pulse beat and to motion from walking, arm swinging, and the like, and does not distinguish between them. The latter is noise, however, insofar as pulse measurement is concerned. Thus, the Stupay patent notes that "the patient must remain quiet to avoid noise input" during the period in which the pulse rate is measured.

Also, if the piezoelectric transducer is not mounted directly over the artery of the user, the pulse signal measured by such devices is of considerably lessened amplitude, and is thus even more likely to be masked by noise. Typically, noise signals may be as high as as 1.0 volts, while the pulse signal may be approximately 0.1 volts. Prior art wristwatch pulsemeters of the piezoelectric transducer type have been inaccurate because of this very unfavorable signal-to-noise ratio. Thus, Cramer U.S. Pat. No. 4,224,948 states that when a piezoelectric transducer is used, "the watch must be worn on the volar surface of the wrist but lateral to the tendon cord bundles," so as to obtain a pulse reading from the radial artery in the subpollex depression; further, "the sensors must be forced into the flesh of the wrist for a reading" and "[t]his situation may be uncomfortable."

Insofar as the inventor is aware, the prior art does not disclose an effective noise-free piezoelectric transducer mechanism for human or animal pulse measurement, which obviates the difficulties described above.

BRIEF DESCRIPTION OF THE DRAWINGS

FIG. 1 shows the wristwatch pulsemeter as viewed when in place on a user's wrist, looking toward the inside of the wrist.

FIG. 2 is a plan view of the underside of the transducer case of the wristwatch pulsemeter.

FIG. 3 is a side view of the case, showing the transducer pressed against the user's wrist.

FIGS. 4A to 4H are cross-sectional side views of the transducer case, showing various transducer configurations.

FIGS. 4J and 4K are details of the piezo-bender and post.

FIG. 5 is a cross-sectional view of the case with a pair of differentially-connected transducers.

FIG. 6 is a plan view, in section, of the case of FIG. 5, as viewed from underneath.

FIG. 7 is a flow chart for the differentially-connected transducer wristwatch pulsemeter.

BRIEF SUMMARY OF THE PRESENT INVENTION

Figure 9:
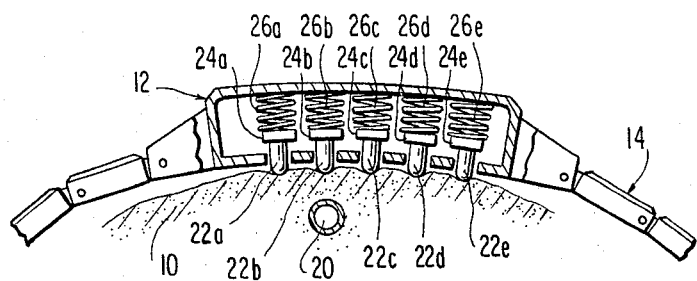
FIG. 9 is a cross-sectional side view of the case of the device shown in FIG. 8.

The invention descried below is intended to lessen or obviate the problems of noise and power consumption, by providing a low-energy-consuming transducer arrangement that substantially eliminates extraneous noise. The use of a piezoelectric element eliminates the power loss attendant to LED and similar devices. The mounting means disclosed herein for the piezoelectric element largely eliminates noise. Use of multiple transducer arrays in which some transducers act as references even further reduces noise, to the point where it is substantially eliminated. The resulting device permits visual or other monitoring of pulse rate in a human or animal body, on a consistent, error-free basis.

DETAILED DESCRIPTION

A perspective view of the simplest contemplated embodiment of the present invention may be seen in FIG. 1, from a vantage point looking toward the inside of a wrist 10 of a user of the device. A transducer housing or case 12 is fastened to a wrist band 14, surrounding the user's wrist and fastened to a digital wristwatch product (containing microprocessor and display). The wristwatch product to which band 14 is attached is not shown in this view, and is concealed by wrist 10. Case 12 has a pair of laterally projecting flanges 16 and 18, which function as a marking device to facilitate the user's placement of band 14 so that the transducer (not shown) within case 12 is placed directly over radial artery 20 of wrist 10. Another appropriate marking device can be used instead of flanges 16 and 18. In this embodiment of the invention, it is desirable to have the transducer as close to directly over the wrist's radial artery as possible, to maximize the signal-to-noise ratio. If the device is used to monitor pulse in a different artery, e.g., one in the human or animal user's leg, the transducer should be as close as possible to a position directly over that artery.

In FIG. 2 the underside of transducer case 12 is shown in plan view. It may be seen that between flanges 16 and 18 is a transducer pulse contact post 22, which is intended to be placed on the skin of the user as closely as possible to directly over the radial artery, and biased against the skin so that it moves in response to the pressure from pulse beats. Post 22 is fastened to a piezoelectric bender transducer element ("piezo-bender") 24, shown in dotted lines. (The mounting of piezo-bender 24 is shown in FIGS. 4A to 4H.) FIG. 3 shows a side view of case 12, in which post 22 projects out from case 12 in the direction of the user's skin and radial artery. Again, piezo-bender 24 is shown in dotted lines.

In FIGS. 4A to 4H, a series of cross-sectional views of transducer cases is shown, with various different configurations for mechanically filtered suspension and mounting of transducers, with which the applicant has experimented. What may be termed a spring mounted dual cantilever arrangement is shown in FIG. 4A. This has been found to be the most advantageous arrangement, so far. In this configuration, post 22 is cemented to piezo-bender 24 on the middle of one face or side (the "lower side," i.e., that closer to the user's skin) thereof; Super Glue is an effective cementing agent. The piezo-bender is elastically mounted to case 12 by means of a pair of upper springs 26 and 28 fastened to the piezo-bender near the ends of the piezo-bender's other face or side (the "upper side," i.e., that farther away from the user's skin). A perspective view of post 22 and piezo-bender 24 is shown in detail in FIG. 4J. Typically, piezo-bender 24 is about 0.5 inch long, 0.06 inch wide, and 0.02 inch thick. (The thickness of piezo-bender 24 is exaggerated in FIG. 4J to facilitate viewing.)

In ordinary operation of the device, as previously indicated, post 22 firmly contacts the skin of the user, above the radial artery. Springs 26 and 28 bias post 22 against the skin. The user's pulse beat presses post 22 upward against piezo-bender 24. Springs 26 and 28 resist the upward motion of post 22, causing piezo-bender 24 to bend and flex, which results in the generation of a signal. The resulting signal is delivered to a microprocessor and display in the pulsemeter, as explained more fully hereafter, via a pair of wires 58a–b soldered to piezo-bender 24, at opposite corners of the piezo-bender "sandwich."

Springs 26 and 28 also act as a mechanical filter for the signal, attenuating and largely eliminating frequencies not passed by the filter. Selection of springs with appropriate physical constants (relatively "soft" springs) permits attenuation of high frequency noise components of the signal generated by piezo-bender 24 without undue loss of the lower major pulse signal frequency components. In contrast, when piezo-bender 24 is suspended rigidly or by relatively "stiff" springs, the noise components are passed and tend to have peaks of 1.0 volts or greater, while pulse signal peaks are about 0.1 volts. Frequencies between 10 and approximately 50 Hz are those of major use in this pulsemeter device, as discussed more fully hereafter, while noise signals caused by body motion and the like tend to be over about 50 Hz. It is therefore desirable to use a low-pass ("soft") spring with a cut-off at about 50 Hz, to eliminate noise due to motion.

In FIG. 4B, another dual cantilever configuration for suspension of piezo-bender 24 is shown. In this configuration, foam pads 30 and 32 replace springs 26 and 28 of FIG. 4A, to anchor, cushion, and filter piezo-bender 24. What may be termed a quadruple spring mounted dual cantilever arrangement is shown in FIG. 4C. In this configuration upper springs 26 and 28 of FIG. 4A are supplemented by a pair of lower springs 34 and 36, which connect the lower side of piezo-bender 24 to case 12 in the same way that upper springs 26 and 28 connect the upper side of piezo-bender 24 to case 12. In FIG. 4D, a pair of "rubberband" tension elements 38 and 40 connect piezo-bender 24 to the lower inside of case 12. These tension elements may also be springs. In all of the configurations shown in FIGS. 4A to 4D, transducer post 22 is mounted to the middle of piezo-bender 24 and the two ends of piezo-bender 24 are suspended with elastic elements. The latter bias post 22 against the user's skin and also filter out some of the higher frequency elements of the force signal applied to the transducer, and of the output voltage signal that it wold otherwise generate.

In FIGS. 4E to 4H, a series of lever mounted transducer configurations are shown. In FIG. 4E, post 22 is fastened near one end of piezo-bender 24, on its lower face, as shown also in detail in FIG. 4K. The other end of piezo-bender 24 is cemented to a rubber mount 42, which is cemented to the inside end of case 12. An upper spring 44 connects the middle of the upper side of piezo-bender 24 to the inside of the top of case 12. In operation, the user's pulse presses post 22 up against piezo-bender 24 against the resistance of spring 44. Piezo-bender 24 flexes and generates a signal as before. A perspective view of the piezo-bender as used in these configurations is shown in FIG. 4K.

In FIG. 4F, piezo-bender 24 cantilevers out from foam pad 46, which is cemented to the inside end of case 12. Post 22 projects down from the free end of piezo-bender 24. In FIG. 4G, a pair of "rubberband" tension elements 48 and 50 connect the lower side of piezo-bender 24 to case 12; again, post 22 projects down from one end of piezo-bender 24. In FIG. 4H, one end of piezo-bender 24 is fastened from below to the inside end of case 12 by a lower spring 52. The middle of piezo-bender 24 is fastened from above to the inside top of case 12 by an upper spring 54. From the free end of piezo-bender 24, post 22 projects down. In all of the configurations shown in FIGS. 4E to 4H, transducer post 22 is mounted to one end of piezo-bender 24 and the other end of piezo-bender 24 is mounted by an elastic element to the transducer case, so that post 22 is biased against the user's skin. The elastic element also filters out some of the undesired (noise) frequencies from the force signal applied to post 22 by the user's pulsebeat.

The useful (non-noise) electrical signal from piezo-bender 24 is typically of the order of magnitude of 0.05 to 0.15 volts. The lower figure is more typical of "at rest" pulse beat, while the higher one is more typical of exercise conditions. Signal magnitude also varies from person to person. Although the repetition frequency of human pulse is on the order of magnitude of 1 Hz, the leading edge of the signal tends to contain frequencies on the order of 10 to 50 Hz. Such frequency components are those that the circuitry described hereafter is intended to process. The signal may advantageously be electronically filtered, to further attenuate over-50 Hz noise frequencies, and this signal may be further processed and used as the input to conventional microprocessor circuitry of the digital watch type. It has been found advantageous to use the filtered pulse signal to drive a standard Schmitt Trigger or a comparator, so that a digital-compatible signal is derived from the pulse beat's analog signal, in order to provide an appropriate input for the microprocessor.

The pulsemeter microprocessor's output may be displayed on a conventional visual display of the digital watch type. Because the microprocessor and its display are substantially that which is used in a conventional digital watch, the present invention may be advantageously used in connection with such watches, as an additional optional feature thereof. Pulsemeter output may also be monitored acoustically or may be monitored by being sampled and stored in a memory device (such as a random access memory ("RAM"), for subsequent analysis. The latter permits observation of a patient's pulse for presence of arrhythmias, over a long period and away from the physician's office.

A more advanced embodiment of the invention is shown in FIG. 5. Here, a pair of piezo-benders 24a and 24b is used. Both are elastically mounted, side by side, but staggered, less than 0.015 inches apart, in a configuration similar to that shown in FIG. 4A, by means of springs 26a, 26b, 28a, and 28b. (The piezo-benders are each shown tipped to one end, in FIG. 5, so that the farther one may be viewed.) Two pairs of signal wires 58a-58b and 60a-60b carry the output signals from piezo-benders 24a and 24b to the electronic circuitry, described hereafter. The wires may advantageously be twisted, to lessen noise pickup, and they exit the transducer case through a tightly grommetted aperture, and pass along the watchband to the electronic circuitry described below, which may advantageously be housed in the watch case. In FIG. 6, a view of the underside of the transducer case is shown in cutaway view, showing the staggered, side-by-side arrangement of the two transducers of FIG. 5, and their respective posts 22a and 22b. As previously indicated, the piezo-benders are approximately 0.5 inch long and 0.06 inch wide.

Post 22a of piezo-bender 24a is placed over radial artery 20, as in the device shown in FIG. 3. Nearby, post 22b of piezo-bender 24b senses substantially the same noise due to motion and the like as does post 22a, but the force of the pulse signal from artery 20 is greatly attenuated at post 22b. An advantageous alternative arrangement of the transducers is shown in FIG. 7. Instead of staggering the transducers longitudinally in order to laterally separate posts 22a and 22b relative to the longitudinal axis of the radial artery, as in FIGS. 5 and 6, this arrangement rotates the transducers in the case by 90 degrees, so that the longitudinal axis of the transducers is now parallel to the longitudinal axis of the radial artery. Consequently, posts 22a and 22b are now laterally separated relative to the longitudinal axis of the radial artery, without need for staggering them. (A similar arrangement for five transducers is shown in FIG. 9.)

Representations of the resulting voltage signals from the two piezo-benders are shown in FIG. 7 as A and B, where A is the voltage signal from the transducer over the radial artery and B is that from the nearby (noise reference) transducer. FIG. 7 further depicts (in flow chart form) the processing of these two signals to produce a visual pulsemeter display. Signals A and B initially both have considerable noise. Much of the noise can be eliminated by an active filtering and amplification stage. Thus, signals A and B are respectively routed through low-pass filter-amplification stages 62a and 62b. The filtered and amplified signals A and B, with components over about 50 Hz largely eliminated, are fed to differential amplifier stage 64.

Almost all of the remaining noise of all frequencies is subtracted out by differential amplifier 64. Voltage signal A may be represented as: $A = K_1(S+N)$, where $K_1$ is a constant associated with the first transducer and amplifier input, S is a radial pulse force signal, and N is the noise force signal due to motion and the like. Similarly, voltage signal B may be represented as: $B = K_2(cS+N)$, where $K_2$ is an amplification constant associated with the second transducer and amplifier input, and c is the attenuation factor constant for the second pulse signal, because the second transducer is not directly over the radial artery. If $K_1$ and $K_2$ are approximately equal, the signal delivered from differential amplifier 64 is approximately K(A-B). Matching the piezo-benders is believed to be the best way to insure that $K_1$ is approximately equal to $K_2$, if the supplier's tolerances are not deemed tight enough (approximately 10% or better). Another way is to balance the two inputs to differential amplifier 64, but this is believed to be a more costly procedure, and is therefore less preferred.

The signal output from amplifier 64 is then routed to an analog-to-digital buffer stage 66, which converts the analog pulse output signal from stage 64 to a digital-compatible signal suitable as an input for a digital watch microprocessor. This conversion may advantageously be effected with a conventional Schmitt Trigger or comparator circuit. The resulting digital-compatible signal is routed to pulse logic and microprocessor stage 68, which converts the analog pulse signal by conventional means to a digital signal representing, as a decimal number, the number of pulse beats per minute that the user's heart delivers to radial artery 20. This number is then displayed on visual display 70. (If acoustic display or other monitoring is desired, different conventional circuitry may be used therefor.)

Figure 8:
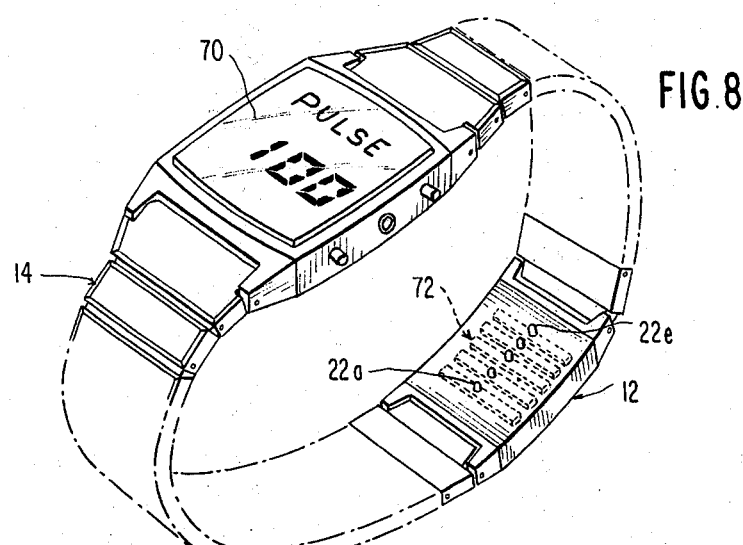
FIG. 8 is a perspective view of a five-transducer wristwatch pulsemeter.

A further embodiment of the invention is shown in FIG. 8. A five-transducer array 72 is used, to make it unnecessary for the user to place the device carefully over the radial artery. Again, the transducer configuration of FIG. 4A is preferred. FIG. 9 shows a sectional view of the transducer case 12, with the five-transducer array 72. The array comprises five posts 22a to 22e, fastened to five piezo-benders 24a to 24e, and elastically suspended by springs or elastic suspension elements 26a to 26e (which are shown in FIG. 9, and elastic suspension elements 28a to 28e which are not shown in FIG. 9). In FIG. 9, post 22b is over the radial artery, and thus picks up the maximal pulse signal. The transducers are arrayed side by side. They are approximately 0.05 inches wide and are spaced about 0.05 inches apart.

Figure 10:
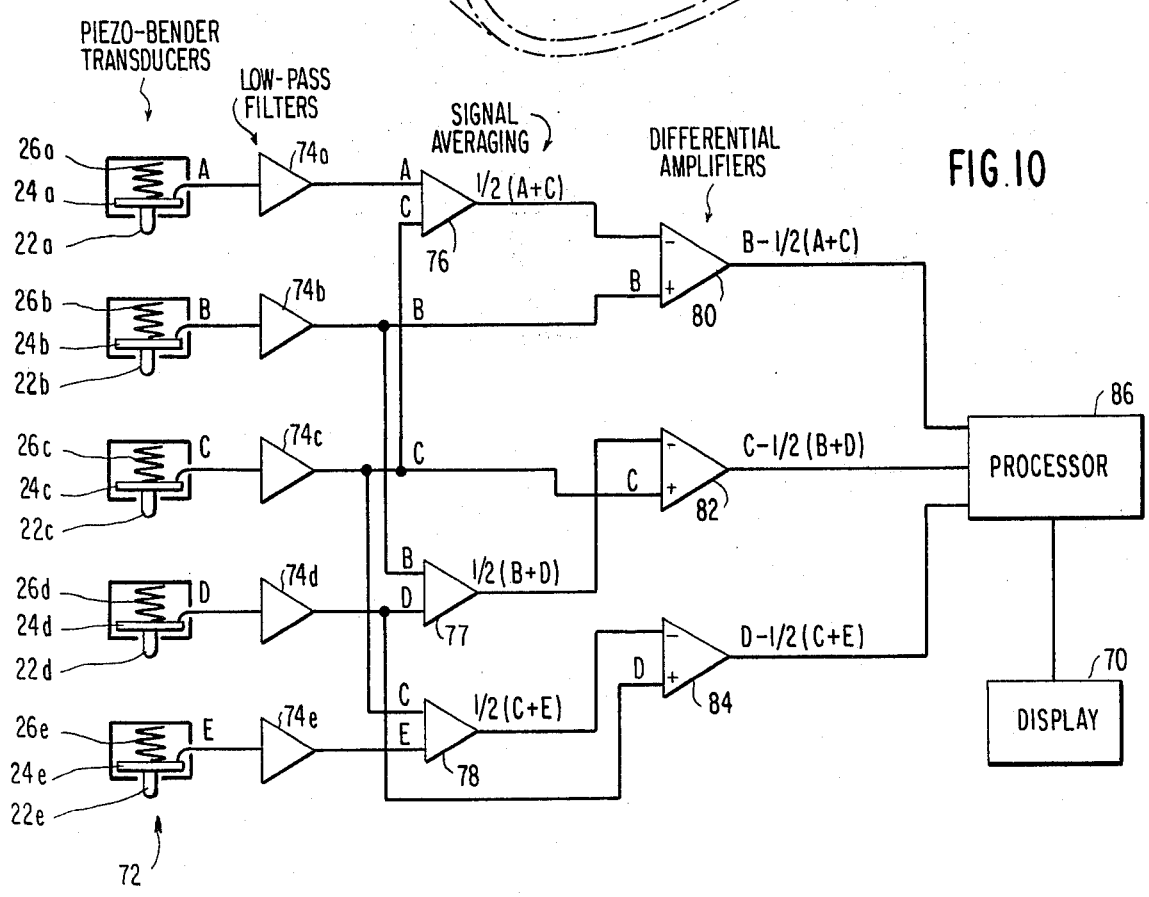
FIG. 10 is a flow chart for the five-transducer wristwatch pulsemeter of FIG. 8.

In FIG. 10, a flow chart for the signals of array 72 is shown. The five transducers produce signals A, B, C, D, and E. Each signal is fed to a low-pass active filter and amplification stage, 74a to 74e. The resulting output signals are then passed to a signal averaging stage. Signals A and C are fed to a signal averager 76, which sums inputs A and C and outputs 0.5(A+C). Similarly, averager 77 outputs 0.5(B+D) and averager 78 outputs 0.5(C+E). These averaged signals are then fed to a set of differential amplifiers to permit subtraction of an averaged noise signal from a noise-plus-pulse signal.

The inputs to differential amplifier 80 are B and 0.5(A+C), and the output is B-0.5(A+C). Thus, this signal is the voltage produced by the pulsebeat signal delivered to transducer post 22b, with noise superimposed on the signal, minus the average of the voltage signal produced by motion at the two adjacent posts 22a and 22c. This average is substantially the same as the noise superimposed on pulsebeat signal B. Similarly, differential amplifiers 82 and 84 produce respective outputs of C-0.5(B+D) and D-0.5(C+E). The arrangement of FIG. 10 therefore produces three possible signals, each of which has the average of the two nearest noise signals subtracted from it. The resulting outputs are fed to logic and microprocessor circuit 86, which selects a pulse signal (here, signal B) and processes it by conventional means into a signal for digital display 70 to show as a numerical representation of the user's pulse rate. The selection is advantageously performed by passing each differential amplifier output signal to a Schmitt Trigger circuit, or a comparator, which amplifies and passes only that signal of sufficient amplitude as exceeds a predetermined threshold value (e.g., equivalent to a 0.04 volt transducer signal). The output of the comparator is adjusted to be at the 0/1 levels required by the digital watch microprocessor.

This arrangement contemplates that one of the three middle transducer posts (22b, 22c, or 22d) will be over the radial artery. If it were contemplated that the extreme end transducer posts (22a and 22e) might also at times be over the radial artery, slightly modified circuitry could be used to provide, also, signals of A or E, minus the average signal of the two nearest transducers, or simply A or E, minus the nearest transducer's signal (B or D, respectively). Analog circuitry was used at this point rather than digital circuitry, but the same kind of result could be obtained by digital means. It may be thought that with this configuration, the radial artery might fall exactly halfway between two transducer posts, e.g., 22b and 22c. It might be thought that the result could be that no pulse could be read. This is not the case, however, in the circuit disclosed here. First, it has not been observed that the device will remain in a position with the radial artery halfway between two transducer posts. The natural notches and grooves of the human wrist appear to cause one of the posts to settle into a depression over the radial artery and to resist being dislodged. Consequently, two posts do not ordinarily rest in locations where both of them pick up a strong pulse signal. In any case, even when two somewhat attenuated pulse signals are fed through the system, there is enough gain available to operate the microprocessor, and there are no double counts or missed counts. The microprocessor input can be fed a substantially squared or flat wave (0/1 voltage level), rather than a pulse, so that if two comparators present overlapping inputs to the microprocessor it counts them as one input.

In the preferred form of this embodiment, as now contemplated, the array of five transducers is in a straight line along the circumference of the user's wrist. The transducers could be staggered in a zig-zag array without adversely affecting the operation of the device. Other such arrangements are also possible, for example, a pentagonal or hexagonal array. It is also possible to use the average of all other transducers as a noise reference, rather than simply the two nearest ones.

More generally, this embodiment contemplates the use of an array comprising a number of transducers. The extreme ends of the array (a and e of FIGS. 8 to 10) are not intended to be placed over the radial artery in operation of the pulsemeter; they are merely present for noise reference purposes. The other transducers in the array may or may not be over the radial artery, depending on how the wristband is placed; only one of these transducers will be directly over the radial artery or closest to the artery. Those transducers that can occupy a position over or near the user's radial artery (b, c, and d of FIGS. 8 to 10) may be termed "potential sensors." The transducer actually closest to the user's radial artery at any particular time, and thus that with the signal of greatest amplitude, may be termed the "actual sensor." The transducers other than the actual sensor, at any particular time, may be termed "non-sensors." Different members of the array of transducers (different potential sensors) will act as the actual sensor if the wrist band is moved or put on the user's wrist differently. One or more of the non-sensors may be used as noise reference. When the average signal obtained from the one or more non-sensors is subtracted from the signal of the sensor, a relatively noise-free pulse signal is obtained. (The average signal of only one non-sensor, as in the embodiment shown in FIGS. 5-7, is the signal of that one transducer.)

EXAMPLE 1

A one transducer pulsemeter was made in accordance with the configuration indicated in FIGS. 2, 3, and 4A. Springs were selected (Associated Spring, Compression Spring No. C0057-006-0250-M) that effectively filtered out force signals over 50 Hz. The piezo-bender was a Model R0505, Gulton Industries, Inc., PZT ceramic piezoelectric bender. Stainless steel insulated lead wires were soldered to the aluminized surfaces of the piezo-bender at opposite corners of the "sandwich," and were then threaded along the watchband to the watch case, as a twisted pair. Peak transducer signals of approximately 0.2 volts and 0.15 second duration were observed, which were fed (after filtering, low-pass 50 Hz) to an amplifier and Schmitt Trigger. The output was then fed to a conventional digital watch type of CMOS chip microprocessor (Motorola MC 146805E2) and conventional 4-digit LCD display. The single-transducer product was tested under exercise conditions and gave repeatable and relatively noise-free readings, when the user was at rest or while he was walking, and when the device was tapped on. It was inaccurate, however, about half the time when the user swung his arms, jogged in place, or jogged in linear motion.

EXAMPLE 2

A dual transducer pulsemeter was made in accordance with the configuration indicated in FIG. 7. The piezo-benders were the same Gulton models, with similar springs and stainless steel leads. The piezo-bender pairs used were matched to within 5%. The low-pass filter-amplification stages 62a-b of FIG. 7 were the two halves of a Linear Design LM082 8-pin dual operational amplifier ("op amp"). Differential amplifier 64 of FIG. 7 was half of another LM082 op amp, while buffer 66 of FIG. 7 was the other half, connected as a Schmitt Trigger. The same microprocessor chip was used.

The product was tested under exercise conditions and gave highly repeatable and noise-free readings, when the device was aligned at or near the radial artery. That is, it was accurate for each of the test conditions referred to in Example 1, including jogging and arm-swinging. But this model can become disaligned in use, which can cause inaccuracy.

EXAMPLE 3

A pulsemeter was made in accordance with the configuration shown in FIGS. 8, 9, and 10. Again, the same model of piezo-bender was used. Three 14-pin Linear Design LM084 quad bi-FET op amps were used for the electronic circuitry, providing up to 12 op amp stages. Five stages were used for filtering and amplification elements 74a-e of FIG. 10; three, for averagers 76, 77, and 78; and three, for differential amplifiers 80, 82, and 84.

Similar tests were performed on the product, with similar results. The device was moved, on the user's wrist, from time to time, in order to disarrange the transducer array. Consistent results were nonetheless obtained. Alignment with respect to the radial artery was unnecessary. Readings under exercise conditions were substantially free of noise. That is, jogging and arm-swinging did not cause inaccuracy.

It will thus be seen that the objects set forth above, among those made apparent from the preceding description, are efficiently attained. Since certain changes may be made in carrying out the above methods, and in the constructions set forth, without departing from the spirit and scope of the present invention, it is intended that all matter contained in the above description and shown in the accompanying drawings shall be interpreted as illustrative and not restrictive.

It is also to be understood that the following claims are intended to cover all of the generic and specific features of the invention which, as a matter of language, might be said to fall therebetween.

What is claimed and desired to be secured by United States Letters Patent is:

1. In a portable pulsemeter worn on the body of a human or animal user, said pulsemeter including:
    at least one piezoelectric transducer in which is a piezoelectric element;
    housing means for mounting said piezoelectric transducer, said housing means being maintained in substantially stationary contact relative to said body, in the vicinity of a region thereof through which an artery passes, and said piezoelectric transducer being adapted to produce transducer output signals representative of forces, among other things, radial to an artery of said user and produced by said user's pulse beat;
    at least one pulse rate monitor which is operated by monitor signals representative of occurrences of the user's pulse beat; and
    means for delivering to said pulse rate monitor monitor signals derived from said transducer output signals, the improvement comprising at least one elastically mounted piezoelectric transducer, in which are:
    a transducer post fastened to said piezoelectric element, said post being adapted to firmly contact said body in the vicinity of said artery; and
    at least one elastic mounting connecting said piezoelectric element to said housing means, the physical constants of said elastic mounting being selected to filter out higher frequency components of the forces applied to said transducer post.

2. The pulsemeter of claim 1 in which the pulsemeter is of the wristwatch type and has as a pulse rate monitor a visual display of the numerical value of the user's pulse rate.

3. The wristwatch pulsemeter of claim 2 in which there is one piezoelectric transducer which is adapted to remain in place near or directly over the user's radial artery.

4. The wristwatch pulsemeter of claim 2 in which there are:
    at least two said elastically mounted piezoelectric transducers, one of said transducers being in closer proximity to the artery than any other one; and
    circuitry means for deriving monitor signals representative of the difference between:
    an output signal of a sensor, said sensor being said elastically mounted piezoelectric transducer that is in closest proximity to said artery, and
    an average output signal derived from at least one other said elastically mounted piezoelectric transducer.

5. The wristwatch pulsemeter of claim 4 in which there are two said elastically mounted piezoelectric transducers, said circuitry means deriving monitor signals representative of the difference between the output signals of said two elastically mounted piezoelectric transducers.

6. The wristwatch pulsemeter of claim 4 in which:
    there are at least three said elastically mounted piezoelectric transducers, slightly separated from one another circumferentially around the user's wrist, and
    said average output signal is derived from the output signals of the two said elastically mounted piezoelectric transducers circumferentially on either side of said sensor and immediately adjacent thereto.

7. The wristwatch pulsemeter of claim 6 in which there are five said circumferentially separated tranducers.

8. The pulsemeter of claim 1 in which:
    selection means are provided for selection of times at which, or pulse signal conditions under which, the user's pulse rate is to be recorded; and
    at least one said pulse rate monitor is a memory having means for storing data representing the numerical value of the user's pulse rate, measured at said selected times or under said selected conditions, and adapted to have the data stored therein unloaded therefrom.

9. The device of claim 8 in which the memory is a random access memory.

10. A method of piezoelectrically monitoring pulse rate in the body of a human or animal subject, and at the same time decreasing the noise contamination in the pulse rate data and permitting display of the thus noise-decontaminated pulse rate data, which comprises:
    (A) providing a monitor containing at least one piezoelectric transducer which
        (1) has fastened thereto contact means adapted to firmly contact said body near an artery thereof and adapted to apply to said piezoelectric transducer a force representative of the pulse beat of said artery; and
        (2) is elastically mounted to said monitor by mounting means having physical constants selected to filter out higher frequency components of forces applied via said contact means to said piezoelectric transducer;
    (B) providing circuitry means intermediate between said piezoelectric transducer and a display means whereby monitor signals representative of occurrences of said pulse beat are produced and can be fed to said display means;
    (C) placing said monitor in substantially stationary contact with said body, near an artery thereof with said contact means in contact with the body; and
    (D) monitoring said pulse beat with said monitor.

11. The method of claim 10 wherein the monitor is of the wristwatch type and the monitoring is a visual display of the numerical value of said subject's pulse rate.

12. The method of claim 10 in which there is a plurality of said piezoelectric transducers and the said contact means of said plurality of piezoelectric transducers are placed in firm contact with said body; and in which said monitor signals produced by said circuitry means are representative of the difference between (i) the output signal derived from the said contact means in closest proximity to said artery and (ii) the average output signal derived from at least one other said contact means.

13. The method of claim 12 in which there are two said piezoelectric transducers, so that said monitor signal is representative of the difference between the respective output signals derived from the said closest contact means and the said other contact means.

14. The method of claim 12 in which:

there are five said piezoelectric transducer, disposed in a substantially linear array around the circumference of the subject's wrist;

the said contact means placed in closest proximity to said artery is one of three central said contact means; and said average output signal is derived from the two said contact means that are circumferentially immediately adjacent to said closest contact means and are on either side thereof.

* * * * *